United States Patent [19]

Orlowski

[11] 4,388,069

[45] Jun. 14, 1983

[54] DENTAL RESTORATIVE MATERIAL

[75] Inventor: Jan A. Orlowski, Altadena, Calif.

[73] Assignee: Blendax-Werke R. Schneider GmbH & Co., Mainz, Fed. Rep. of Germany

[21] Appl. No.: 368,743

[22] Filed: Apr. 15, 1982

[51] Int. Cl.³ .............................................. A61K 6/08
[52] U.S. Cl. ..................................... 433/228; 106/35; 260/998.11; 433/199; 433/201; 523/116; 523/117
[58] Field of Search .................. 106/35; 523/115–117, 523/120; 260/998.11; 433/228, 199, 201

[56] References Cited

U.S. PATENT DOCUMENTS 3,629,187 12/1971 Waller .................................. 523/115
3,709,866 1/1973 Waller ............................. 204/159.23
4,177,563 12/1979 Schmitz-Josten et al. .......... 523/116
4,302,376 11/1981 Walkowiak et al. ................ 523/117

Primary Examiner—Lorenzo B. Hayes
Attorney, Agent, or Firm—Connolly and Hutz

[57] ABSTRACT

Dental restorative material containing polymerizable (meth)acrylic compounds in admixture with amorphous and crystalline fillers.

7 Claims, No Drawings

DENTAL RESTORATIVE MATERIAL

The present invention refers to a new dental restoring material containing a special filler mixture.

Dental filling materials on the basis of polymerizable compounds, so-called "composites", contain obligatorily a mineral filler in addition to one or several polymerizable monomers, activators, optionally polymerization catalysts and other components.

According to its composition and quantity this filler determines the physical properties of the dental filling made by the composite. The higher the filler amount and its particle size, the better are the physical properties, the worse, however, usually the polishability.

Thus, it has been tried to improve the polishability of such materials by using fillers with small particle sizes between approx. 10 and 300 m$\mu$; however, this resulted in a decrease of the mechanical properties.

These so-called "microfillers" are mostly or almost exclusively used in the preparation of so-called light-curing composites, i.e. dental restoring materials being composed of one phase and containing fillers, polymerizable compounds and a polymerization initiator forming radicals when exposed to light.

This is particularly due to the fact that these materials have to show a certain depth of cure which cannot be reached with most of the fillers of higher particle sizes, the so-called "macrofillers".

Other macrofillers that do not have this disadvantage cause discolorations with the polymerization (=curing) of the filling. This applies particularly to the different kinds of glass resulting in a greenish or grayish discoloration during the cure of the filling.

Moreover, these fillings are not polishable.

Thus, a necessity existed to develop dental restoring materials, especially light-curing materials, not showing these disadvantages but being well curable without polymerization catalysts when exposed to light, i.e. having a satisfactory depth of cure, no discoloration but good physical properties particularly with respect to reduced water sorption, shrinkage, a low coefficient of thermal expansion tending to zero and improved mechanical properties especially regarding hardness and diametrical tensile strength.

Moreover, it is desirable to achieve at least a certain degree of polishability.

According to the present invention, it has been found that a dental restoring material with the above referred properties may be prepared by incorporating as an inorganic filling material in a quantity of approx. 60 to approx. 90% by weight or the total composition a mixture composed of at least one optionally silanized amorphous filler, preferably in a quantity of approx. 50 to approx. 75% by weight of the filler mixture, at least one optionally silanized crystalline filler, preferably in a quantity of approx. 10 to 50, especially approx. 25 to approx. 50% by weight of the filler mixture with an average particle size each between approx. 0.3 and approx. 40 microns, preferably 0.3 and 20 microns. This mixture may contain up to approx. 10% by weight of an optionally silanized microfiller, especially finely divided silica with an average particle diameter of up to approx. 0.2 microns to improve polishability.

Suitable amorphous filling materials are especially various vitrous glasses like lithium aluminum silicate glass, powdered quartz, borosilicate glass, barium aluminum silicate, barium aluminum borate silicate, or glass ceramics with particle sizes between approx. 0.5 and approx. 40, preferably between 1 and 20 microns. These amorphous fillers as a part of the filler mixture used according to the invention may be x-ray transparent or x-ray opaque. A summary of such suitable filling materials is given, e.g., by R. L. Bowen, Journal of Dental Research, Vol. 58/5 (May 1979), p. 1493–1501, especially p. 1495–1498.

Suitable x-ray opaque fillers are particularly described in the U.S. Pat. Nos. 3,801,344, 3,808,170 and 3,975,203 as well as in the Published German Patent Application (Offenlegungsschrift) No. 2,347,591.

The preferred crystalline filling compound in the mixture according to the invention is crystalline aluminum silicate, e.g. obtained from precipitated sodium feldspar. Further appropriate crystalline filler components are e.g. lithium aluminum silicate like Beta-eucryptite, synthetic or natural calcium silicate etc., with an average particle size between approx. 0.3 and 40 microns, preferably approx. between 0.3 or 0.5, resp., and 20 or 10 microns, resp..

To improve the incorporability of the filler mixture according to the invention into the complete composition and the compatibility with its organic components, it is advisable to silanize these fillers with an organosilane. The silanization may be effected by any suitable organosilane of the general formula

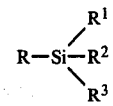

R, R$^1$, R$^2$, R$^3$ being the same or different organic residues provided that at least one residue is an OH-group or a residue that can be converted into an OH-group, e.g. by hydrolysis, particularly an alkoxy group. Preferred organosilanes are (meth)acrylpropyl dihydroxymethoxysilane, (meth)acroylpropyl hydroxydimethoxysilane, (meth)acroylpropyl trimethoxysilane or their mixtures; but also vinyl triethoxysilane or vinyl tri(methoxyethoxy)silane are examples for suitable silanization agents.

To improve the polishability of the dental restoring material according to the invention, a certain amount of a microfiller, especially finely divided silica with an average particle diameter below 200 m$\mu$ may be added. However, the amount of this microfiller should not exceed 10% by weight of the total filler amount to avoid a negative influence on the good physical properties of the cured material. Preferably 4 to 8, especially approx. 6% by weight of the total filler mixture are composed of said finely divided silica. This microfiller is preferably silanized. An appropriate silanized silica filling material is described in our co-pending application, Ser. No. 304,647.

A particularly suitable filler mixture is composed of 50 to approx. 75% by weight of optionally silanized amorphous lithium aluminum silicate with a particle size between approx. 1 and approx. 35 microns (on average approx. 5 microns) and approx. 25 to approx. 50% by weight of an optionally silanized crystalline aluminum silicate with an average particle size between approx. 0.3 and approx. 20 microns, especially 0.5 to 1 microns on average, preferably in a weight proportion of 3:1.

As described above, the dental restoring materials according to the invention are especially suitable for use as light-curing products, i.e. products which are present in one phase and polymerize when exposed to light.

Such compositions contain one or more photo-polymerization initiators. Particularly suitable for this purpose are carbonyl compounds like benzoin and its derivatives, especially benzoin methyl ether, benzil and benzil derivatives, e.g. 4,4-oxydibenzil or other dicarbonyl compounds, e.g. diacetyl, 2,3-pentanedione or metal carbonyls, quinone or their derivatives. The amount of photo-polymerization initiators is approx. 0.01 to approx. 5 weight % of the total composition.

These light-curing, e.g. photo-polymerizable preparations contain preferably so-called polymerization accelerators. These are substances accelerating the polymerization reaction when polymerization iniators are present. Known accelerators are e.g. amines, like p-toluidine, N,N-dimethyl-p-toluidine, N,N-di(hydroxyethyl)-p-toluidine, trialkylamines like trihexyl amine, polyamines like N,N,N',N'-tetraalkylalkylene diamines, barbituric acid, and dialkyl barbituric acids and sulfimides, preferably in an amount of approx. 0.01 to approx. 5% by weight of the total composition. Suitable accelerators are e.g. described in G. M. Brauer et al., Journal of Dental Research, Vol. 58/No. 10 (1979), p. 1994-2000.

A preferred light-curing dental restoring material contains approx. 60 to approx. 90% by weight of the total composition of an inorganic filler mixture, consisting of approx. 60 to approx. 75% by weight (calculated on the filler mixture) of a preferably silanized amorphous filler, especially lithium aluminum silicate with a particle size between approx. 1 and approx. 20 microns, and approx. 25 to approx. 40% by weight of a preferably silanized crystalline filler, especially aluminum silicate with a particle size of approx. 0.5 to approx. 1 microns. This filler mixture may contain up to 10, preferably up to approx. 6% by weight of a preferably silanized finely divided silica with an average particle size below 0.2 microns.

In principle it is also possible to apply the dental restoring materials according to the invention as preparations being present in two separate phases, one phase containing a polymerization catalyst, e.g. a peroxide, and the other phase containing an accelerator for this peroxide, e.g. an organic amine. Mixing of the 2 phases is effected immediately before the filling of the tooth, polymerization taking place in the open cavity to be filled, preferably provided with a reliner or a bonding agent.

Appropriate peroxides decomposing under formation of radicals when polymerization is initiated are e.g. acyl peroxides like benzoyl peroxide, cumol hydroperoxide, urea peroxide, tert.-butyl hydroperoxide or perbenzoate and silyl peroxides, preferably in amounts of approx. 0.01 to approx. 5, especially approx. 0.5 to 2.5% by weight of the total composition.

If one phase of these separate-phase compositions contains a polymerization initiator, it is advisable to add to the other phase an accelerator of the above described type, preferably an amine or a barbituric acid or its derivatives, e.g. a dialkyl barbituric acid.

In principle, all compounds proposed and suitable for this purpose can be used as polymerizable monomers in the dental restoring materials according to the invention.

Especially the known reaction products obtained from bisphenols, particularly Bisphenol A, and glycidyl methacrylate, known as "Bis-GMA", the various alkandiol dimethacrylates like 1,6-hexanediol methacrylate, 1,4-butanediol dimethacrylate, tri- or tetraethyleneglycol dimethacrylate, bis-(2-methacroylpropyl) phtalate, isophtalate or terephtalate, trimethylolpropane di- and trimethacrylate, as well as especially the reaction products obtained from diisocyanates and hydroxyalkyl methacrylates, as are e.g. described in German Published Patent Application ("Offenlegungsschrift") No. 2,312,559, adducts obtained from (di)isocyanates and 2,2-propane bis-3-(4-phenoxy)-1,2-hydroxypropane-1-methacrylate according to the U.S. Pat. No. 3,629,187 as well as especially the adducts obtained from isocyanates and methacroylalkyl ethers, alkoxybenzenes and alkoxycycloalkanes, resp., as are described in European Published Patent Application No. 44,352 shall be mentioned as suitable examples.

Of course, also mixtures of suitable monomers may be used.

Finally, it is advisable to add UV-stabilizers to dental filling materials based on macromolecular compounds to avoid darkening of the fillings. An especially appropriate UV-stabilizer is 2-hydroxy-4-methoxy benzophenone. Another preferred material is 2-(2'-hydroxy-5'-methylphenyl) benzotriazole; however, in principle each UV-absorbing agent being physiologically inert is suitable for this purpose. Hydroquinone, p-benzoquinone, p-butyl hydroxytoluene etc. may be mentioned examplarily. The latter compound may also act as antioxidant in the cured filling.

A survey of the substances usually used in dental filling materials is given in the article by R. L. Bowen in Journal of Dental Research, Vol. 58/5 (May 1979), p. 1493 and 1503, as well as in the supplements thereto by J. F. Lann, p. 1504 to 1506.

To adjust the appearance of the filled tooth areas as natural as possible, composite materials may contain a small amount of dyes or pigments.

The following examples are illustrating the present invention.

| Mixture A | | |
|---|---|---|
| Reaction product of glycidyl methacrylate and Bisphenol A (Bis-GMA) | | 80% by weight |
| 1,6-Hexanediol dimethacrylate | | 20% by weight |
| Benzil | 0.75 | parts by weight/ |
| Diethylaminoethyl methacrylate (DEAEM) | 0.75 | 100 parts Mixture A |
| 2-(2'-Hydroxy-5'-methylphenyl) benzotriazole | 0.4 | |

| Mixture B | | |
|---|---|---|
| Bis-GMA | | 70% by weight |
| 1,6-hexanediol dimethacrylate | | 18% by weight |
| Trimethylolpropane trimethacrylate | | 12% by weight |
| Benzil | 0.5 | parts by weight/ 100 parts |
| DEAEM | 0.4 | Mixture B |

| Mixture C | |
|---|---|
| Bis-GMA | 66.5% by weight |
| 1,6-Hexanediol dimethacrylate | 25% by weight |
| Ethoxylated Bisphenol A | |

-continued

| Mixture C | |
|---|---|
| dimethacrylate (EBA) | 3.5% by weight |
| Methylene-4,4', N,N'—biscyclohexyl carbamoyl 2-hydroxypropoxytoluene | 1.5% by weight |
| Triethyleneglycol dimethacrylate | 3.5% by weight |
| Benzil | 0.66 parts by weight/100 parts by weight Mixture C |
| DEAEM | 0.82 |
| 2-(2'-Hydroxy-5'-methylphenyl)benzotriazole | 0.13 |

EXAMPLES

The examples I to III are not showing compositions according to the prior art and not falling within the scope of invention.

EXAMPLE I

| Mixture A | 100 parts by weight |
|---|---|
| Amorphous quartz powder (particle size ~5 microns) | 330 parts by weight |
| Properties of the cured material: | |
| Depth of cure: | 3,2 mm. |
| Polishability: | None. |
| Appearance: | Non-satisfactory; highly transparent, greenish. |

EXAMPLE II

| Mixture B | 100 parts by weight |
|---|---|
| Silanized amorphous quartz powder (particle size ~5 microns) | 125 parts by weight |
| Silanized silica (particle size ~20,5 millimicrons) | 45 parts by weight |
| Properties of the cured material: | |
| Depth of cure | 2,5 mm |
| Polishability: | Good. |
| Appearance: | Fairly. The cured material showed yellowish color. |

EXAMPLE III

| Mixture C | 100 parts by weight |
|---|---|
| Lithium aluminum silicate glass, particle size 1 to 35 microns, 4 microns on average | 500 parts by weight |
| Properties of the cured material: | |
| Depth of cure: | 5.0 mm |
| Polishability: | None. |
| Appearance: | Too transparent, greyish. |

The examples 1 to 7 are compositions according to the invention.

EXAMPLE 1

| Mixture A | 100 parts by weight |
|---|---|
| Silanized amorphous quartz powder (average particle size below 5 microns) | 250 parts by weight |
| Crystalline lithium aluminum silicate (particle size 1 to 35 microns, 4 microns on average) | 100 parts by weight |
| Properties of the cured material: | |
| Depth of cure: | 3.7 mm |
| Polishability: | Good. |
| Appearance: | Excellent; the optical properties of the cured material are corresponding to natural tooth structure without discoloration. |

EXAMPLE 2

| Mixture B | 100 parts by weight |
|---|---|
| Silanized borosilicate glass (particle size 0,5 to 35 microns, 3 microns on average) | 450 parts by weight |
| Silanized crystalline aluminum silicate (average particle size 0,5 to 1 microns) | 150 parts by weight |
| Properties of the cured material: | |
| Depth of cure: | 4,0 mm |
| Polishability: | Good. |
| Appearance: | Excellent. The optical properties of the cured material are corresponding to those of natural tooth structure without discoloration. |

EXAMPLE 3

| Mixture C | 100 parts by weight |
|---|---|
| Lithium aluminum silicate glass (particle size 1 to 35 microns, 4 microns on average) | 450 parts by weight |
| Silanized crystalline aluminum silicate (average particle size 0,5 to 1,5 microns) | 150 parts by weight |
| Properties of the cured material: | |
| Depth of cure: | 4,2 mm |
| Polishability: | Good. |
| Appearance: | Excellent. The optical properties of the cured material are corresponding to those of natural tooth structure without discoloration. |

EXAMPLE 4

| Mixture C | 100 parts by weight |
|---|---|
| Silanized borosilicate glass (particle size 0,5 to 35 microns, 3 microns on average) | 450 parts by weight |
| Crystalline lithium aluminum silicate (Beta-Eucryptite) (average particle size 1 micron) | 100 parts by weight |
| Properties of the cured material: | |
| Depth of cure: | 4,4 mm |
| Polishability: | Good. |
| Appearance: | Excellent. The optical properties of the cured material are corresponding to those of natural tooth structure without discoloration. |

EXAMPLE 5

| Mixture B | 100 parts by weight |
|---|---|
| Silanized amorphous quartz powder | |

| -continued | |
|---|---|
| (particle size <5 microns) Silanized crystalline lithium aluminum silicate (Beta-Eucryptite) (average particle size 1 micron) | 150 parts by weight |
| | 150 parts by weight |
| Silanized precipitated silica (particle size 30 to 150 millimicrons) | 20 parts by weight |
| Properties of the cured material: | |
| Depth of cure: | 3,6 mm |
| Polishability: | Excellent. |
| Appearance: | Good, no discoloration detectable. |

EXAMPLE 6

| Mixture C | 100 parts by weight |
|---|---|
| Lithium aluminum silicate (particle size 1 to 35 microns, 4 microns on average) | 250 parts by weight |
| Crystalline aluminum silicate (average particle size 0,5 to 1 microns) | 250 parts by weight |
| Properties of the cured material: | |
| Depth of cure: | 3,1 mm |
| Polishability: | Good. |
| Appearance: | Satisfactory; slightly more opaque than natural tooth structure. |

EXAMPLE 7

| Mixture C | 100 parts by weight |
|---|---|
| Lithium aluminum silicate glass (particle size 1 to 35 microns, 4 microns on average) | 500 parts by weight |
| Crystalline lithium aluminum silicate (Beta-Eucryptite) (average particle size 1 micron) | 60 parts by weight |
| Properties of the cured material: | |
| Depth of cure | 5,5 mm |
| Polishability: | Satisfactory. |
| Appearance: | Satisfactory; a little bit transparent. |

The depth of cure was determined by a curing lamp (type "Translux") after 40 seconds exposure.

The results prove the superiority of the dental restoring compositions according to the invention.

I claim:

1. Dental restoring material containing at least one polymerizable (meth)acrylic compound and 60 to 90% by weight of the total composition of filler mixture of inorganic filler compounds, the filler mixture consisting essentially of
    (a) 50 to 90% by weight, of the filler mixture, of an amorphous filling material,
    (b) 10 to 50% by weight, of the filler mixture, of crystalline aluminum silicate, crystalline calcium silicate or a mixture thereof with both crystalline compounds having an average particle size from about 0.3 to 20 microns, and
    (c) up to 10% by weight, of the filler mixture, of a microfiller with an average particle size of not more than 200 millimicrons.

2. Dental restoring material according to claim 1 wherein at least one of the filler mixture components is silanized.

3. Dental restoring material according to claim 2 wherein component (b) of the filler mixture is silanized aluminum silicate, silanized calcium silicate or a mixture thereof.

4. Dental restoring material according to claim 1 wherein the filler mixture is about 50 to about 75% by weight of amorphous lithium aluminum silicate, about 25 to about 50% by weight of crystalline aluminum silicate, both having an average particle size of less than 0.1 microns.

5. Dental restoring materials according to claim 4 wherein at least one of the filler mixture components is silanized.

6. A light-curable dental restoring material containing at least one polymerizable (meth)acrylic compound and about 60 to about 90% by weight of the total composition of a filler mixture of inorganic filling materials consisting essentially of
    (a) 60 to 75% by weight of an amorphous filling material with a particle size from 1 to 20 microns and
    (b) 25 to 40% by weight of a crystalline filling material selected from the group consisting of aluminum silicate, calcium silicate and mixtures thereof with a particle size from 0.5 to 1 microns, and
    (c) up to 10% by weight, of the filler mixture, of a finely divided silica having an average particle size of less than 0.2 microns.

7. A light-curable dental restoring material according to claim 6 wherein at least one of the inorganic filling materials is silanized.

* * * * *